US012778674B2

(12) United States Patent
Bach et al.

(10) Patent No.: US 12,778,674 B2
(45) **Date of Patent: *Nov. 3, 2026**

(54) ELECTRODE APPARATUS FOR NERVE DENERVATION OR MODULATION IN VIVO

(71) Applicant: DEEPQURE INC., Seoul (KR)

(72) Inventors: Du Jin Bach, Gyeonggi-do (KR); Seok Hyeon Jo, Gyeonggi-do (KR)

(73) Assignee: DEEPQURE INC., Seoul (KR)

( * ) Notice: Subject to any disclaimer, the term of this patent is extended or adjusted under 35 U.S.C. 154(b) by 385 days.

This patent is subject to a terminal disclaimer.

(21) Appl. No.: 18/684,414

(22) PCT Filed: Aug. 18, 2021

(86) PCT No.: PCT/KR2021/010954
§ 371 (c)(1),
(2) Date: Jul. 29, 2024

(87) PCT Pub. No.: WO2023/022249
PCT Pub. Date: Feb. 23, 2023

(65) Prior Publication Data
US 2025/0331916 A1 Oct. 30, 2025

(30) Foreign Application Priority Data
Aug. 18, 2021 (KR) ........................ 10-2021-0108645

(51) Int. Cl.
*A61B 18/12* (2006.01)
*A61B 18/14* (2006.01)
(Continued)

(52) U.S. Cl.
CPC ........ *A61B 18/1492* (2013.01); *A61N 1/0551* (2013.01); *A61B 2017/00314* (2013.01);
(Continued)

(58) Field of Classification Search
CPC ............ A61B 18/1482; A61B 18/1492; A61B 2018/00196; A61B 2018/00434;
(Continued)

(56) References Cited

U.S. PATENT DOCUMENTS

2012/0172864 A1* 7/2012 Farin ...................... A61B 18/14 606/33
2015/0141810 A1* 5/2015 Weadock ................. A61N 7/02 606/49
(Continued)

FOREIGN PATENT DOCUMENTS

KR 10-2013-0108401 A 10/2013
KR 10-2015-0021632 A 3/2015
(Continued)

OTHER PUBLICATIONS

International Search Report issued for International Application No. PCT/KR2021/010954 dated May 16, 2022, 5 pages.
(Continued)

*Primary Examiner* — Daniel W Fowler
(74) *Attorney, Agent, or Firm* — Merchant & Gould P.C.

(57) ABSTRACT

An electrode apparatus for nerve denervation or modulation in vivo includes a main body including a shaft; an electrode unit formed to be drawn out from one end of the shaft and configured to denervate or modulate at least part of nerves on a tube in a body; an electrode guide coupled to the end of the electrode unit and configured to guide the electrode unit to be brought into contact with the tube in the body; an electrode guide driving unit configured to move the electrode guide in forward and backward directions; and an electrode driving unit configured to move the electrode guide in the forward and backward directions in conjunction with the electrode guide driving unit.

12 Claims, 7 Drawing Sheets

(51) Int. Cl.

| | |
|---|---|
| ***A61N 1/05*** | (2006.01) |
| *A61B 17/00* | (2006.01) |
| *A61B 18/00* | (2006.01) |
| *A61M 25/01* | (2006.01) |

(52) U.S. Cl.
CPC ............... *A61B 2017/00318* (2013.01); *A61B 2018/00434* (2013.01); *A61M 25/0138* (2013.01)

(58) Field of Classification Search
CPC ...... A61B 2018/142; A61B 2018/1475; A61B 2018/1465
See application file for complete search history.

(56) References Cited

U.S. PATENT DOCUMENTS

| | | | | |
|---|---|---|---|---|
| 2019/0133681 | A1 | 5/2019 | Jeong | |
| 2021/0338307 | A1* | 11/2021 | Baril | A61B 90/70 |

FOREIGN PATENT DOCUMENTS

| | | | |
|---|---|---|---|
| KR | 10-2015-0101290 | A | 9/2015 |
| KR | 10-2016-0007087 | A | 1/2016 |
| KR | 10-1590005 | B1 | 1/2016 |
| KR | 10-2017-0058964 | A | 5/2017 |
| KR | 10-2018-0094955 | A | 8/2018 |
| KR | 10-2018-0102899 | A | 9/2018 |
| KR | 10-2219632 | B1 | 2/2021 |
| KR | 10-2244131 | B1 | 4/2021 |
| WO | 2015004667 | A1 | 1/2015 |
| WO | 2021040431 | A1 | 3/2021 |

OTHER PUBLICATIONS

European Extended Search Report received for EP Application No. 21954296.6; Mar. 27, 2025; 10 pgs.

* cited by examiner

ELECTRODE APPARATUS FOR NERVE DENERVATION OR MODULATION IN VIVO

TECHNICAL FIELD

The present disclosure relates to an electrode apparatus for nerve denervation or modulation in vivo.

BACKGROUND

A denervation is a surgical procedure intended to control an abnormally overactive autonomic nervous system by damaging specific nerves. For example, a renal denervation can treat hypertension and heart diseases by damaging renal sympathetic nerves directed to the kidney, and a pulmonary denervation can treat lung diseases by damaging parasympathetic nerves directed to the lung.

Nerves usually enclose the outer walls of tubes, such as blood vessels, bronchial tubes, etc., and it may be necessary to enclose the outer walls of tubes to measure signals from the nerves or transmit electrical impulses or various energies to the nerves to damage or destroy the nerves. For example, when a surgical procedure is performed on the renal artery, the main renal artery which is a procedure target has a diameter of from 5 mm to 7 mm, and the accessory renal artery having a diameter of from 1 mm to 2 mm may also be a procedure target. Also, the artery with distributed nerves varies in size from person to person and has different sizes depending on the location.

When the surgical procedure is performed as described above, it is important to delicately locate a component including an electrode to be formed at the end of a catheter so as to enclose the outer wall of the artery. Specifically, in order to effectively denervate or modulate the nerves, the component needs to enclose the outer wall of the artery with distributed nerves in a circumferential direction. Also, it is necessary to reliably and rapidly enclose the artery with the component including the electrode. In particular, it is important to safely and accurately adhere the electrode-formed component to the outer wall of the tube in the body so as not to damage the tube in the body, which can be easily damaged by external stimuli.

DISCLOSURE OF THE INVENTION

Problems to be Solved by the Invention

The present disclosure is conceived to provide an electrode apparatus having a component that guides a plurality of unit elements to enclose the circumference of a tube in the body.

Also, the present disclosure is conceived to provide an electrode apparatus configured to accurately bring a component including an electrode into close contact with an outer wall of the tube in the body without damaging the tube which can be easily damaged by external stimuli.

The problems to be solved by the present disclosure are not limited to the above-described problems. There may be other problems to be solved by the present disclosure.

Means for Solving the Problems

According to an aspect of the present disclosure, an electrode apparatus for nerve denervation or modulation in vivo includes a main body including a shaft; an electrode unit formed to be drawn out from one end of the shaft and configured to denervate or modulate at least part of nerves on a tube in a body; an electrode guide coupled to the end of the electrode unit and configured to guide the electrode unit to be brought into contact with the tube in the body; an electrode guide driving unit configured to move the electrode guide in forward and backward directions; and an electrode driving unit configured to move the electrode guide in the forward and backward directions in conjunction with the electrode guide driving unit. The electrode driving unit includes a tensile force maintenance unit connected to one end of the electrode unit and configured to provide a tensile force to the electrode unit; and a moving unit that moves in the forward direction until the electrode guide is transitioned to a first state in a state where the moving unit is connected to the tensile force maintenance unit, and then is disconnected from the tensile force maintenance unit and further moves in the forward direction until the electrode guide is transitioned to a second state.

The above-described aspects are provided by way of illustration only and should not be construed as liming the present disclosure. Besides the above-described embodiments, there may be additional embodiments described in the accompanying drawings and the detailed description.

Effects of the Invention

According to any one of the above-described aspects of the present disclosure, an electrode driving unit can be located to gradually bring an electrode unit into close contact with a tube together with an electrode guide.

Further, the electrode driving unit can adjust the degree of close contact of the electrode unit with the tube, and, thus, it is possible to accurately bring a component including an electrode into close contact with an outer wall of the tube in the body without damaging the tube which can be easily damaged by external stimuli.

BEST MODE FOR CARRYING OUT THE INVENTION

Figure 1:
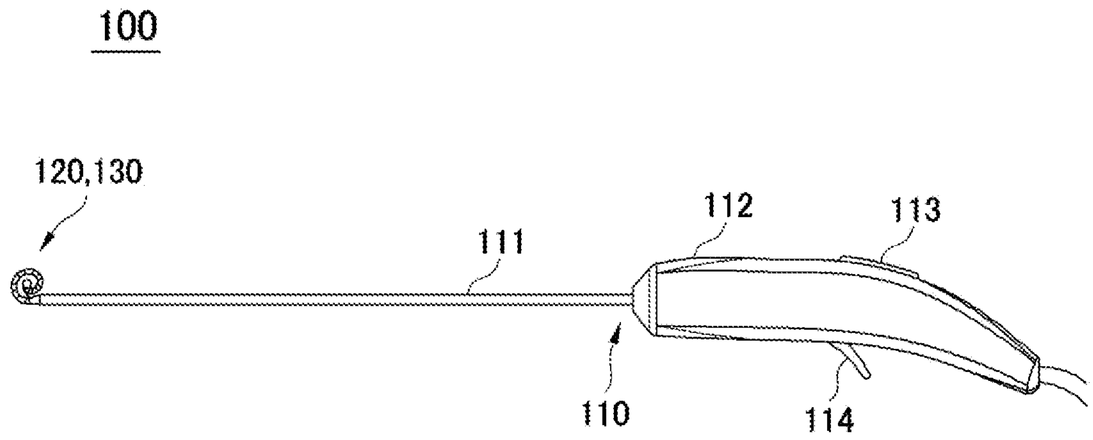
FIG. 1 is a side view of an electrode apparatus according to an embodiment of the present disclosure.

Hereafter, example embodiments will be described in detail with reference to the accompanying drawings so that the present disclosure may be readily implemented by those skilled in the art. However, it is to be noted that the present disclosure is not limited to the example embodiments but can be embodied in various other ways. In the drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element. Further, it is to be understood that the term "comprises or includes" and/or "comprising or including" used in the document means that one or more other components, steps, operation and/or existence or addition of elements are not excluded in addition to the described components, steps, operation and/or elements unless context dictates otherwise and is not intended to preclude the possibility that one or more other features, numbers, steps, operations, components, parts, or combinations thereof may exist or may be added.

Through the whole document, the term "unit" includes a unit implemented by hardware, a unit implemented by software, and a unit implemented by both of them. One unit may be implemented by two or more pieces of hardware, and two or more units may be implemented by one piece of hardware.

Through the whole document, a part of an operation or function described as being carried out by a terminal or device may be carried out by a server connected to the terminal or device. Likewise, a part of an operation or function described as being carried out by a server may be carried out by a terminal or device connected to the server.

Hereinafter, an exemplary embodiment of the present disclosure will be described in detail with reference to the accompanying configuration views or process flowcharts.

Figure 2:
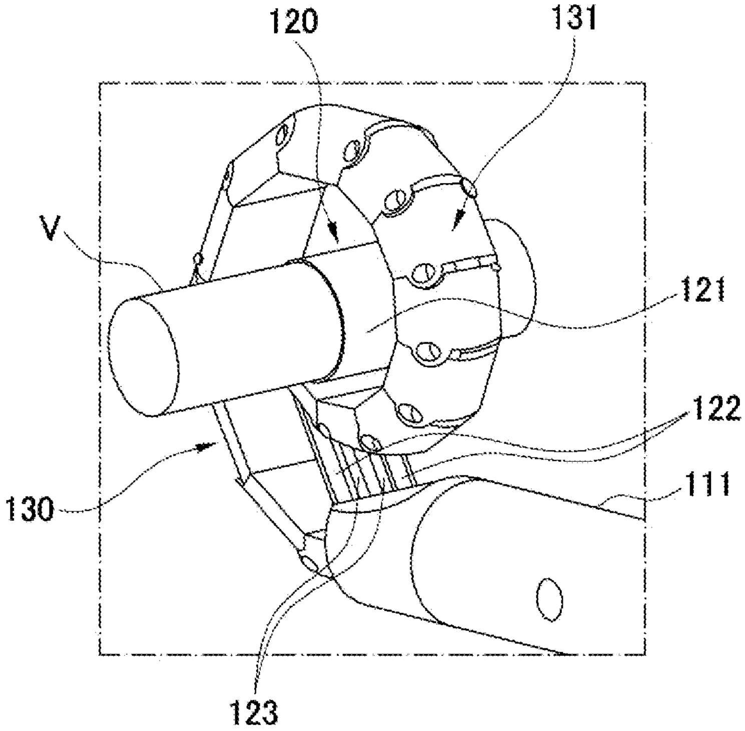
FIG. 2 illustrates a state where an electrode guide illustrated in FIG. 1 guides and locates an electrode unit to enclose a blood vessel according to an embodiment of the present disclosure.
Figure 3A:
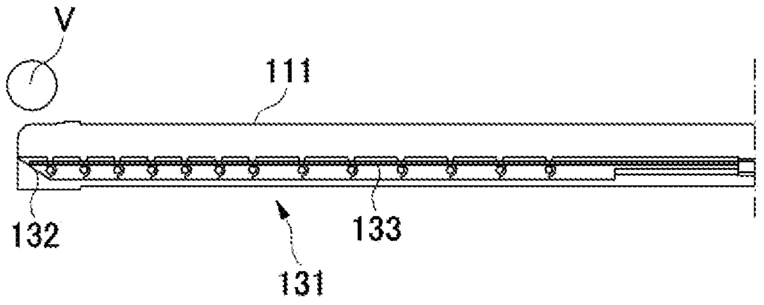
FIG. 3A illustrates an operation process of the electrode guide according to an embodiment of the present disclosure.
Figure 3B:
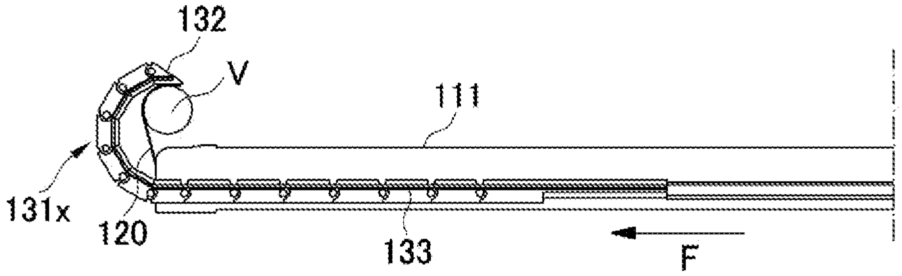
FIG. 3B illustrates an operation process of the electrode guide according to an embodiment of the present disclosure.
Figure 3C:
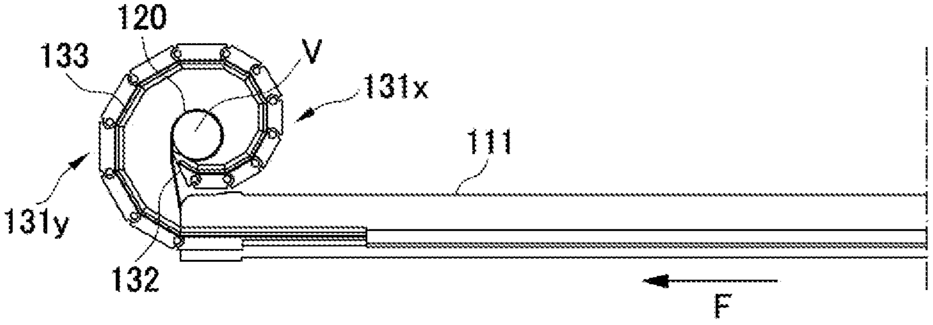
FIG. 3C illustrates an operation process of the electrode guide according to an embodiment of the present disclosure.
Figure 3D:
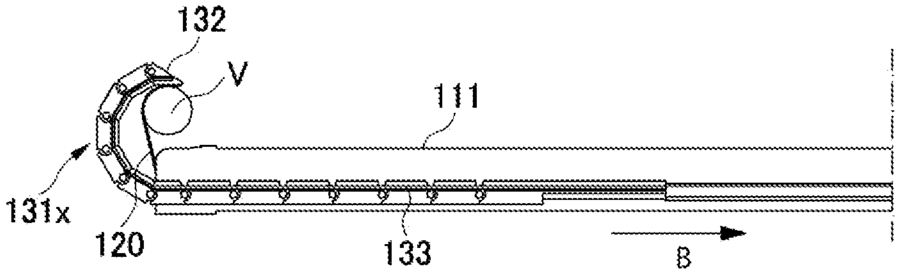
FIG. 3D illustrates an operation process of the electrode guide according to an embodiment of the present disclosure.
Figure 4:
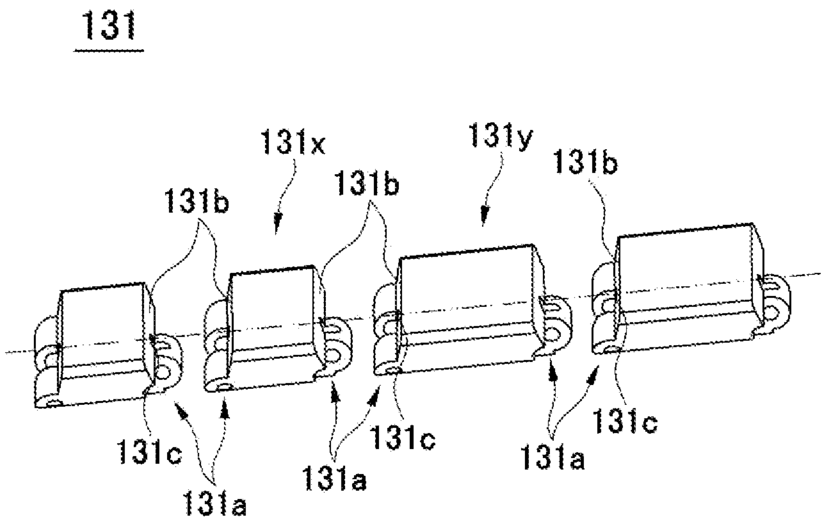
FIG. 4 is an exploded perspective view illustrating a portion of joint units illustrated in FIG. 2.
Figure 5:
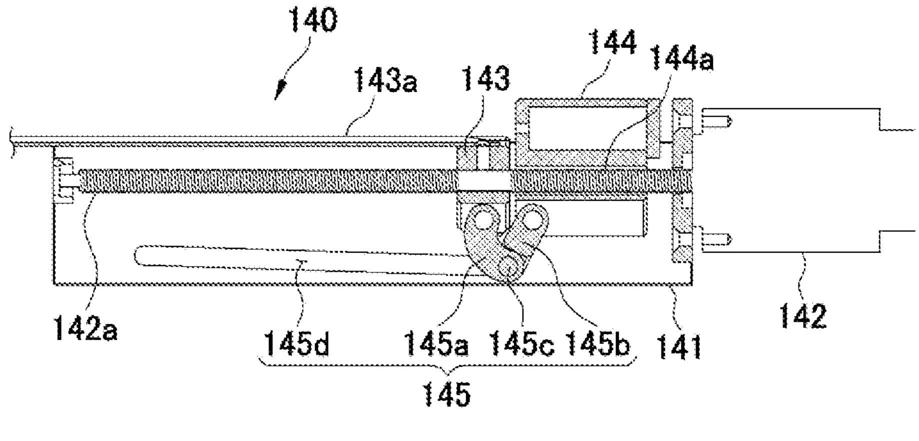
FIG. 5 is a cross-sectional view of an electrode guide driving unit located inside a main body illustrated in FIG. 1.

FIG. 1 is a side view of an electrode apparatus according to an embodiment of the present disclosure. FIG. 2 illustrates a state where an electrode guide illustrated in FIG. 1 guides and locates an electrode unit to enclose a blood vessel according to an embodiment of the present disclosure and FIG. 3A through FIG. 3D illustrate an operation process of the electrode guide according to an embodiment of the present disclosure. FIG. 4 is an exploded perspective view illustrating a portion of joint units illustrated in FIG. 2 and FIG. 5 is a cross-sectional view of an electrode guide driving unit located inside a main body illustrated in FIG. 1. FIG. 6A through FIG. 6F illustrate an operation process of an electrode driving unit according to an embodiment of the present disclosure and FIG. 7 is an example diagram provided to explain the electrode driving unit according to another embodiment of the present disclosure.

Referring to FIG. 1, the electrode apparatus 100 includes the main body 110, the electrode unit 120 and the electrode guide 130, the electrode guide driving unit 140 and the electrode driving unit 150 disposed inside the main body 110.

The main body 110 may include a shaft 111 extending in one direction, a grip portion 112 connected to the shaft 111 so as to be gripped by an operator, a guide manipulation unit 113 formed on the grip portion 112 so as to manipulate an operation of the electrode guide 130, and an electrode manipulation unit 114 formed on the grip portion 112 so as to manipulate energy transfer to the electrode unit 120.

The components for driving and controlling the electrode unit 120 and the electrode guide 130 may be located inside the main body 110. For example, the electrode guide driving unit 140 configured to drive and control the electrode guide 130 and the electrode driving unit 150 configured to drive and control the electrode unit 120 may be disposed inside the main body 110.

The electrode unit 120 is formed to be drawn out from one end of the shaft 111 and configured to denervate or modulate at least part of nerves distributed on a tissue in the body including a tube depending on manipulation by the operator. The electrode unit 120 is accommodated inside the shaft 111 and when the electrode apparatus 100 operates, the electrode unit 120 can be drawn out by means of the electrode guide 130 which will be described later.

Referring to FIG. 2, the electrode unit 120 may include a base unit 121, an electrode unit 122 and a sensor unit 123. In the electrode apparatus 100, an electrode encloses an outer surface of a tube or tube-shaped tissue V in the body and energy can be transferred through the electrode. To this end, the base unit 121 may be formed as a flexible printed circuit board (PCB).

The electrode unit 122 may be composed of two electrodes extending parallel to each other on the base unit 121 on the base unit 121. In the present embodiment, the base unit 121 and the electrode unit 122 may be configured to extend in a circumferential direction and enclose the tube in the body or the like.

The electrode unit 122 may be made of a material such as stainless steel or gold, which is harmless to the human body and conducts electricity well, in order to block or denervate or control or modulate the nerves.

Also, the electrode unit 122 may transfer various types of energy from an energy source generator. For example, the energy may include radio-frequency (RF) energy, electrical energy, laser energy, ultrasonic energy, high-intensity focused ultrasound energy, cryogenic energy and other heat energy.

Also, the electrode unit 122 may be implemented as a flexible PCB for transferring RF energy, a transducer for transferring ultrasonic energy or a metal electrode for transferring high-voltage energy and thus may transfer energy to damage the nerves.

Further, the sensor unit 123 may be formed on the base unit 121. For example, the sensor unit 123 may be a thermocouple that measures a temperature by contacting with the tube in the body or the like, and when neurotomy is performed with the electrode apparatus 100, the sensor unit 123 may monitor a temperature of a treatment site. As another example, the sensor unit 123 may measure signals from the nerves on the tube.

The sensor unit 123 may be, for example, a thermocouple composed of a pair of copper and constantan.

The electrode guide 130 functions to bring the electrode unit 120 into contact with the tube in the body. The electrode guide 130 is coupled to the electrode unit 120 and deformed into a wound state to bring the electrode unit 120 into contact with the tube in the body.

Referring to FIG. 2 through FIG. 4, the electrode guide 130 includes a plurality of joint units 131. The plurality of joint units 131 forms a curved winding path P to enclose the circumference of the tube V in the body with the electrode unit 120 interposed therebetween. The state illustrated in FIG. 2 and FIG. 3C may be a state where the plurality of joint units 131 is disposed along the curved winding path P.

Referring to FIG. 3A through FIG. 3D, the electrode guide 130 may further include a tip joint 132 and a wire 133. The tip joint 132 may support the electrode unit 120 and may be coupled to the end of the plurality of joint units 131 connected sequentially to each other.

The tip joint 132 may be drawn out from one end of the shaft 111 earlier than the plurality of joint units 131. As illustrated in FIG. 3C, the tip joint 132 may be located close to the tube V in the body and may have a tapered shape that gradually decreases in width or thickness toward the end in order to suppress interference with the electrode unit 120 or maximize the surface enclosing the tube in the body. The end of the electrode unit 120 may be fastened and fixed to the tip joint 132.

The wire 133 may be formed to sequentially penetrate the plurality of joint units 131. Referring to FIG. 4, each joint unit 131 may have a through-hole 131*c* in a longitudinal direction to allow penetration of the wire 133.

The end of the wire 133 sequentially penetrating the through-holes 131*c* may be coupled and fixed to the tip joint 132, and the wire 133 can slide with respect to each joint unit 131 in the through-hole 131*c* in the longitudinal direction.

Therefore, the wire 133 can guide the plurality of joint units 131 and the tip joint 132 to be located on the winding path and provide a force of pulling the plurality of joint units 131 and the tip joint 132 in a direction to be wound around the tube V.

The wire 133 may be operated to protrude from one end of the shaft 111 together with to the plurality of joint units 131. Here, the wire 133 may be designed to protrude less than the plurality of joint units 131 per unit time and thus can provide a force of pulling the plurality of joint units 131 along a curved path.

Each join unit 131 may include hinge units 131*a* and winding support units 131*b*. The hinge units 131*a* are configured for rotatable connection to adjacent joints and may be formed on one or both sides of the joint unit 131 in the longitudinal direction in which the joint units 131 are connected parallel to each other.

As illustrated in FIG. 4, the hinge unit 131*a* may have a rotation axis in a direction intersecting the longitudinal direction so as to be connected to the hinge unit 131*a* of the adjacent joint unit 131. A hinge pin (not illustrated) may be inserted into and fastened to each hinge unit 131*a* in the direction of the rotation axis.

The winding support units 131*b* are configured to support the plurality of joint units 131 on the winding path and may be formed on one or both sides of the joint unit 131 in the longitudinal direction to support the adjacent joint unit 131.

As illustrated in FIG. 2 and FIG. 4, the winding support unit 131*b* may be located adjacent to the hinge unit 131*a* in an inward direction of the electrode guide 130 (in a direction of winding the joint unit 131).

For example, the winding support unit 131*b* may be formed as a surface having a predetermined angle and area and supported by the adjacent winding support unit 131*b* in surface contact with each other, and, thus, a wound shape of the electrode guide 130 can be maintained.

The winding support unit 131*b* and the wire hole 131*c* may be formed at locations spaced apart from a rotation center of the hinge unit 131*a* in an inward direction toward the tube V in the body.

When the wire 133 is pulled backwards relative to the electrode guide 130 (when a length of the wire 133 drawn out from the shaft 111 is smaller than that of the joint units 131), a tensile force may be applied to the wire 133 in a direction of winding the electrode guide 130. On the other hand, the winding support units 131*b* may provide a force of supporting the joint units 131 to each other in a direction of suppressing winding of the electrode guide 130. Since the wire 133 and the winding support units 131*b* form a balanced force in opposite directions, the electrode guide 130 can be fixed on the winding path.

Further, the electrode guide 130 may include a first joint group 131*x* and a second joint group 131*y*. That is, the plurality of joint units 131 may be divided into the first joint group 131*x* and the second joint group 131*y* having different lengths.

Due to a difference in length, the first joint group 131*x* may form a first radius of curvature and the second joint group 131*y* may form a second radius of curvature greater than the first radius of curvature. As can be seen from FIG. 3C, the joint units (the first joint group 131*x*) having a relatively small length may form a smaller radius of curvature and the joint units (the second joint group 131*y*) having a relatively great length may form a greater radius of curvature.

When the joint units 131 located close to the tip joint 132 form a path having a smaller radius of curvature, a path along which the tip joint 132 enters a space between the tube in the body and the shaft 111 may be formed as shown in FIG. 3C. Also, the electrode guide 130 including the joint units 131 may have an overall spiral shape.

Referring to FIG. 3A through FIG. 3D, the electrode guide 130 is accommodated together with the electrode unit 120 inside the shaft 111 and may protrude from one end in a forward direction F while being deformed into the wound state at the time of surgical procedure.

For example, when the plurality of joint units 131 is sequentially drawn out, the plurality of joint units 131 may move along the curved winding path due to a difference in displacement from the wire 133 and thus may overall enclose the tube V.

Further, the electrode guide 130 is spaced apart from an outer circumferential surface of the tube and the electrode unit 120 located inside the wound electrode guide 130 may be in close contact with the outer circumferential surface of the tube V.

The plurality of joint units 131 may be drawn out from the shaft 111 by means of the electrode guide driving unit 140 and wound in a direction to enclose the tube V. Accordingly, a space where the electrode guide 130 operates can be minimized, and an operation of denervating or modulating nerves can be performed safely and accurately in a narrow space.

Referring to FIG. 5, the electrode guide driving unit 140 may be configured to move the electrode guide 130 in forward and backward directions, and may include a frame 141, a motor unit 142, a rod block 143, a wire block 144 and a variable connection unit 145.

The frame 141 may be provided to be fixed inside the main body and may include a guide slot or guide shaft extending in the forward and backward directions.

The motor unit 142 may be connected to the frame 141 and may rotate a rotation shaft 142*a* rotatably supported by the frame 141. For example, the motor unit 142 may receive electrical energy to rotate the rotation shaft 142*a*.

One end of the rod block 143 may be connected to the joint unit 131. The rod block 143 may be moved in the forward and backward directions by means of the motor unit 142. Specifically, the rod block 143 may be moved in the forward and backward directions in engagement with the rotation shaft 142*a* extending in the forward and backward directions and having a thread thereon.

The rod block 143 may include a rod 143*a*, which is located inside the shaft 111 and extends in one direction (forward and backward directions) and supports the joint units 131, and a corrugated component slidably coupled to the guide slot or guide shaft of the frame 141.

In addition to the above-described rotation shaft 142*a* and motor unit 142, the electrode guide driving unit 140 according to the present disclosure may be configured to move the rod block 143 in the forward and backward directions by various linear actuation mechanisms. For example, the electrode guide driving unit 140 may include a linear actuator of cylinder type including a pneumatic, hydraulic or electric linear actuator, or a piezoelectric or ultrasonic linear actuator.

The wire block 144 may be formed to support the wire 133 and moved in the forward and backward directions in conjunction with the rod block 143. The wire block 144 may include a corrugated component slidably inserted into the guide slot or guide shaft and a sliding hole 144*a* slidably accommodating the rotation shaft 142*a*, and may move in the forward and backward directions in parallel to the rod block 143

The variable connection unit 145 may connect the rod block 143 and the wire block 144 to each other and vary a distance between the rod block 143 and the wire block 144. To this end, the variable connection unit 145 may include a rod link 145*a*, a wire link 145*b*, a hinge pin 145*c* and a pin slot 145*d*.

The rod link 145*a* and the wire link 145*b* may be rotatably connected to the rod block 143 and the wire block 144, respectively. Also, the rod link 145*a* and the wire link 145*b* may be rotatably connected to each other by the hinge pin 145*c*.

The pin slot 145*d* is formed to slidably accommodate the hinge pin 145*c*. Specifically, the pin slot 145*d* is formed to extend at a predetermined tilt angle with respect to the forward and backward directions. The pin slot 145*d* may be formed in the frame 141.

Meanwhile, the electrode unit 120 may be drawn out from the shaft 111 by means of the electrode driving unit 150 and may be wound in the direction to enclose the tube V by means of the electrode guide 130. Specifically, the electrode unit 120 may move together with the electrode guide 130 in the forward direction along the curved winding path and may be gradually brought into close contact with the tube V in the body under the control of the electrode driving unit 150. Therefore, in a state where the electrode unit 120 is stably in contact with the tube V in the body without damaging the tube V in the body, an operation of denervating or modulating nerves can be performed.

Figure 6A:
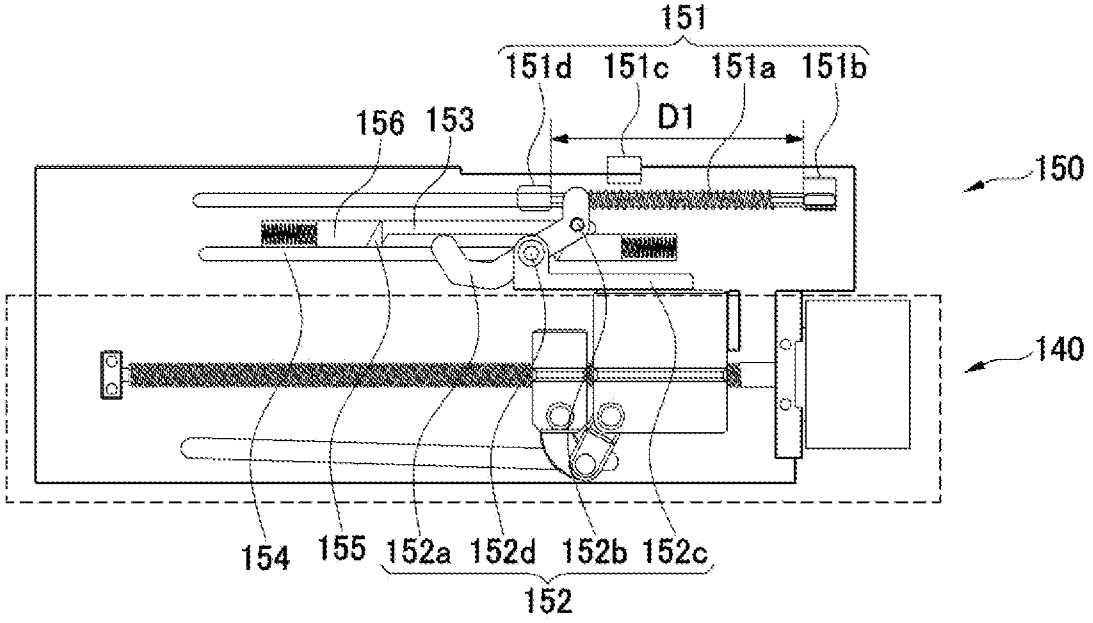
FIG. 6A illustrates an operation process of an electrode driving unit according to an embodiment of the present disclosure.
Figure 7:
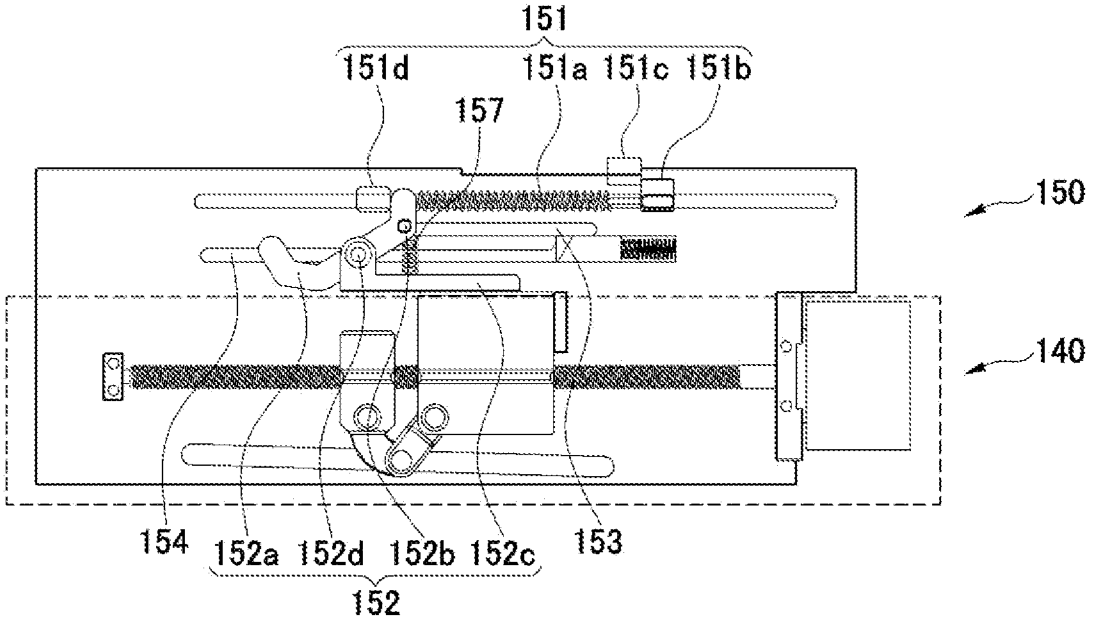
FIG. 7 is an example diagram provided to explain the electrode driving unit according to another embodiment of the present disclosure.

Referring to FIG. 6A, the electrode driving unit 150 may be configured to move the electrode unit 120 in the forward and backward directions in conjunction with the electrode guide driving unit 140. The electrode driving unit 150 may include a tensile force maintenance unit 151, a moving unit 152, a forward movement rail 153, a backward movement rail 154, a connection rail 155 connecting the forward movement rail 153 and the backward movement rail 154, and a second stopper 156. The backward movement rail 154 may be configured to move a pin 152*b* of the moving unit 152 in the backward direction in order to transition the electrode guide 130 from a second state to a first state. Herein, the first state is a state right before the electrode guide 130 is drawn out from one end of the shaft 111 as illustrated in FIG. 3A, and may be a state right before the electrode guide 130 encloses the circumference of the tube V in the body. Otherwise, the first state may be a state before the electrode guide 130 fully encloses the circumference of the tube V as illustrated in FIG. 3B and FIG. 3D.

The second state may be a state where the electrode guide 130 fully encloses the circumference of the tube V in the body as illustrated in FIG. 3C. The backward movement rail 154 according to the present disclosure may have a greater length than the forward movement rail 153.

The tensile force maintenance unit 151 may be connected to one end of the electrode unit 120 and may provide a tensile force to the electrode unit 120. The tensile force maintenance unit 151 may include a first spring 151*a*, a protrusion 151*b* protruding from one side, a first stopper 151*c* and an electrode connection portion 151*d* on the other side.

The first spring 151*a* may provide a tensile force to the electrode unit 120, and the first stopper 151*c* may block movement of the protrusion 151*b* when the tensile force maintenance unit 151 moves in the forward direction to generate the tensile force of the first spring 151*a*.

The electrode connection portion 151*d* may be connected to one side of the electrode unit 120 and transfer the tensile force of the first spring 151*a* to the electrode unit 120.

The electrode connection portion 151*d* may further move in the forward direction until the tensile force maintenance unit 151 and the moving unit 152 are disconnected from each other and the electrode guide 130 is transitioned to the second state.

Specifically, even when the moving unit 152 is disconnected from the tensile force maintenance unit 151, the moving unit 152 can move in the forward direction through the connection rail 155 and the backward movement rail 154. Here, after forward movement of the protrusion 151*b* is blocked by the first stopper 151*c*, only the electrode connection portion 151*d* further moves in the forward direction until the electrode guide 130 is transitioned from the first state to the second state. This is because the end of the electrode guide 130 is connected to the end of the electrode unit 120.

Therefore, after the tensile force maintenance unit 151 is disconnected from the moving unit 152 and the protrusion 151*b* is supported by the first stopper 151*c*, the tensile force is provided to the electrode unit 120. Accordingly, while the electrode guide 130 is transitioned from the first state to the second state, the electrode unit 120 may be gradually brought into contact with the tube V. FIG. 6C illustrates an example where the protrusion 151*b* is supported by the first stopper 151*c* right after the tensile force maintenance unit

151 is disconnected from the moving unit 152, and, thus, the tensile force is provided to the electrode unit 120.

The moving unit 152 being connected to the tensile force maintenance unit 151 may move in the forward direction until the electrode guide 130 is transitioned to the first state. After the moving unit 152 is disconnected from the tensile force maintenance unit 151, the moving unit 152 may further move in the forward direction until the electrode guide 130 is transitioned to the second state.

The moving unit 152 may include a connection portion 152*a* for connection to the tensile force maintenance unit 151, the pin 152*b*, a support 152*c* and a hinge 152*d*.

The pin 152*b* may be formed on one side of the connection portion 152*a*, and may move in the forward direction along the forward movement rail 153 or may move in the forward or backward direction along the backward movement rail 154. Therefore, the moving unit 152 may move together with the tensile force maintenance unit 151 in the forward direction along the forward movement rail 153 through the pin 152*b*, and after the moving unit 152 is disconnected from the tensile force maintenance unit 151, the moving unit 152 may further move in the forward direction along the backward movement rail 154 until the electrode guide 130 is transitioned to the second state. Then, the moving unit 152 may move in the backward direction to transition the electrode guide 130 from the second state to the first state.

The support 152*c* may be connected to the electrode guide driving unit 140. For example, the support 152*c* may be connected to the wire block 144.

The hinge 152*d* is configured to make the connection portion 152*a* rotate, and when the pin 152*b* moves from the forward movement rail 153 to the connection rail 155, the hinge 152*d* rotates and the connection portion 152*a* may be disconnected from the tensile force maintenance unit 151. Therefore, after the connection portion 152*a* is disconnected from the tensile force maintenance unit 151, each of the electrode unit 120 and the electrode guide 130 may move.

Specifically, after the tensile force maintenance unit 151 is disconnected from the moving unit 152, the moving unit 152 further moves in the forward direction until the electrode guide 130 is transitioned to the second state. Thus, a tensile force of the first spring 151*a* may be gradually generated. The generated tensile force of the first spring 151*a* may be transferred to the electrode unit 120. Therefore, in the electrode apparatus 100 according to the present disclosure, the electrode unit 120 can be gradually brought into close contact with the tube V in the body to suppress damage to the tube V.

Also, according to the present disclosure, even after the electrode unit 120 is in close contact with the tube V, the operator can control forward or backward movement of the electrode guide 130 through the guide manipulation unit 113 and thus can adjust the degree and position of close contact of the electrode unit 120 with the tube V in the body. Therefore, the electrode apparatus 100 according to the present disclosure can accurately bring a component including an electrode into close contact with the tube V in the body.

When the pin 152*b* moves in the backward direction, the second stopper 156 may suppress the pin 152*b* not to move again along the connection rail 155. The second stopper 156 may block the connection rail 155 when the pin 152*b* is located on the backward movement rail 154 through the connection rail 155.

Hereafter, driving of the electrode unit 120 by means of the electrode driving unit 150 will be described with reference to FIG. 6A through FIG. 6F. FIG. 6A through FIG. 6F illustrate states corresponding to the states illustrated in FIG. 3A through FIG. 3D.

The electrode driving unit 150 and the electrode guide driving unit 140 illustrated in FIG. 6A may be in a state right before forward movement starts or right after backward movement ends. Therefore, as illustrated in FIG. 3A, the electrode unit 120 and the electrode guide 130 may be in a state right before enclosing the circumference of the tube V in the body or right after the electrode unit 120 and the electrode guide 130 having enclosed the circumference of the tube V in the body are transitioned to the state before enclosing the tube V. That is, the electrode unit 120 and the electrode guide 130 may be in a state right before or right after neurotomy is performed with the electrode apparatus 100.

Figure 6B:
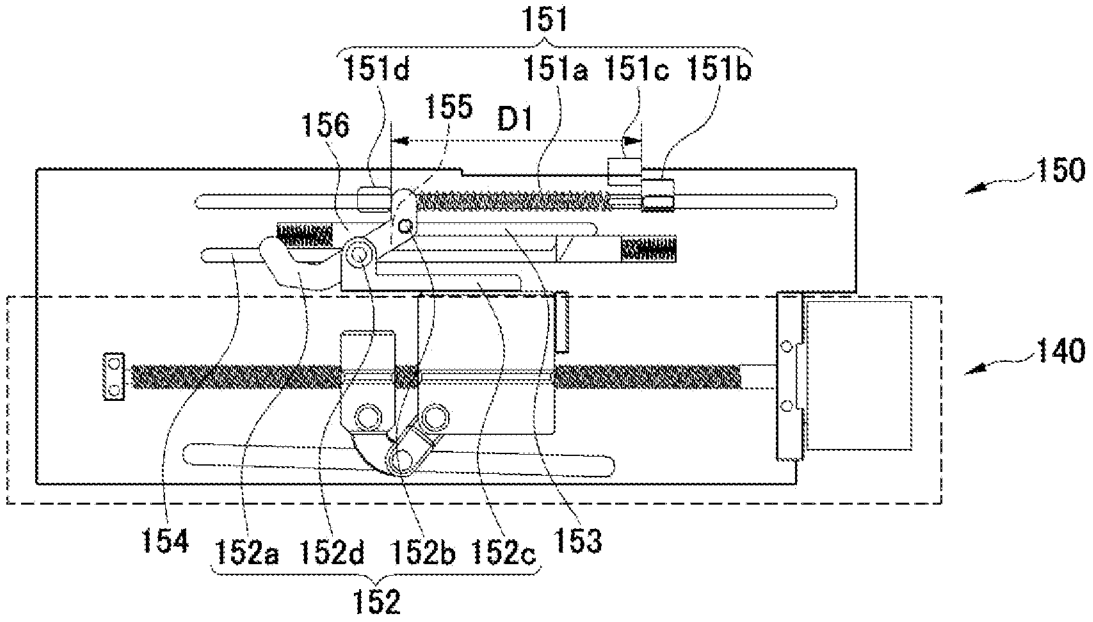
FIG. 6B illustrates an operation process of the electrode driving unit according to an embodiment of the present disclosure.
Figure 6C:
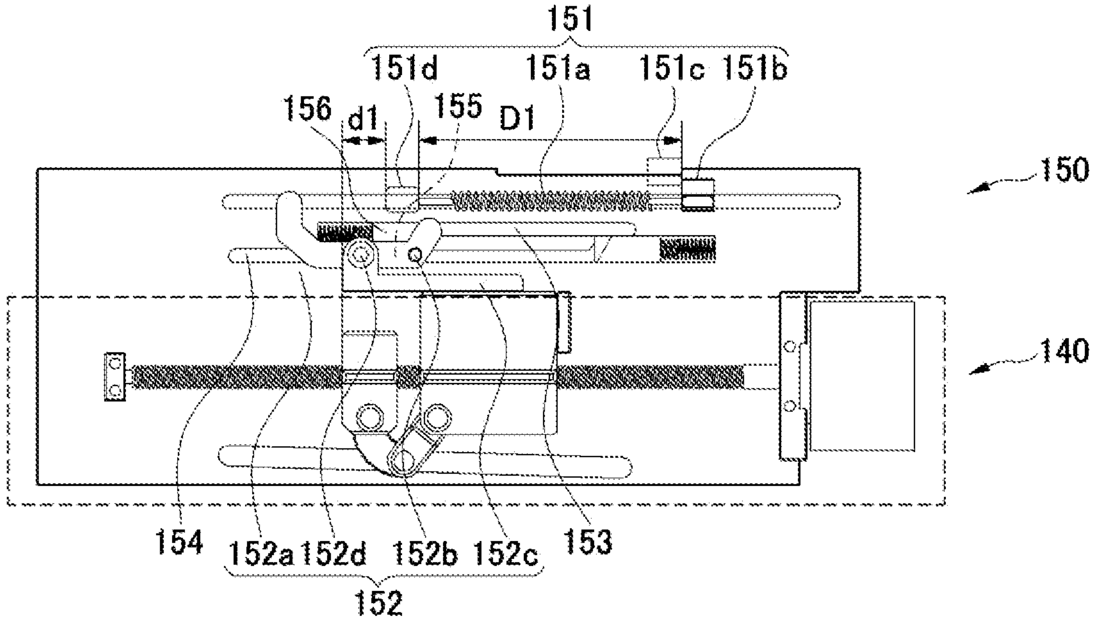
FIG. 6C illustrates an operation process of the electrode driving unit according to an embodiment of the present disclosure.

Referring to FIG. 6B, the electrode driving unit 150 may move in the forward direction along a path provided by the forward movement rail 153 together with the electrode guide driving unit 140 moving in the forward direction. Due to forward movement of the electrode driving unit 150 and the electrode guide driving unit 140, the electrode unit 120 and the electrode guide 130 may be transitioned from the state illustrated in FIG. 3A to the state illustrated in FIG. 3B, i.e., may be drawn out from the shaft 111 in the forward direction F and wound to enclose the circumference of the tube V in the body.

Specifically, when the electrode guide driving unit 140 is moved in the forward direction by driving of the motor unit 142, the tensile force maintenance unit 151 is also moved in the forward direction through the moving unit 152.

That is, as the electrode guide driving unit 140 moves in the forward direction, the pin 152*b* of the moving unit 152 connected to the electrode guide driving unit 140 may move in the forward direction along the forward movement rail 153. Here, the electrode guide 130 is drawn out from the shaft 111 in the forward direction F and the tensile force maintenance unit 151 connected to the moving unit 152 moves in the forward direction, and, thus, the electrode unit 120 of which one end is connected to the electrode connection portion 151*d* may also be drawn out from the shaft 111.

Here, the first stopper 151*c* of the tensile force maintenance unit 151 may block movement of the protrusion 151*b* when the tensile force maintenance unit 151 moves in the forward direction. Referring to FIG. 6B, forward movement of the protrusion 151*b* on one side of the tensile force maintenance unit 151 moving together with the electrode guide driving unit 140 in the forward direction is blocked by the first stopper 151*c*, but the electrode connection portion 151*d* on the other side of the tensile force maintenance unit 151 may move together with the moving unit 152 in the forward direction.

Figure 6D:
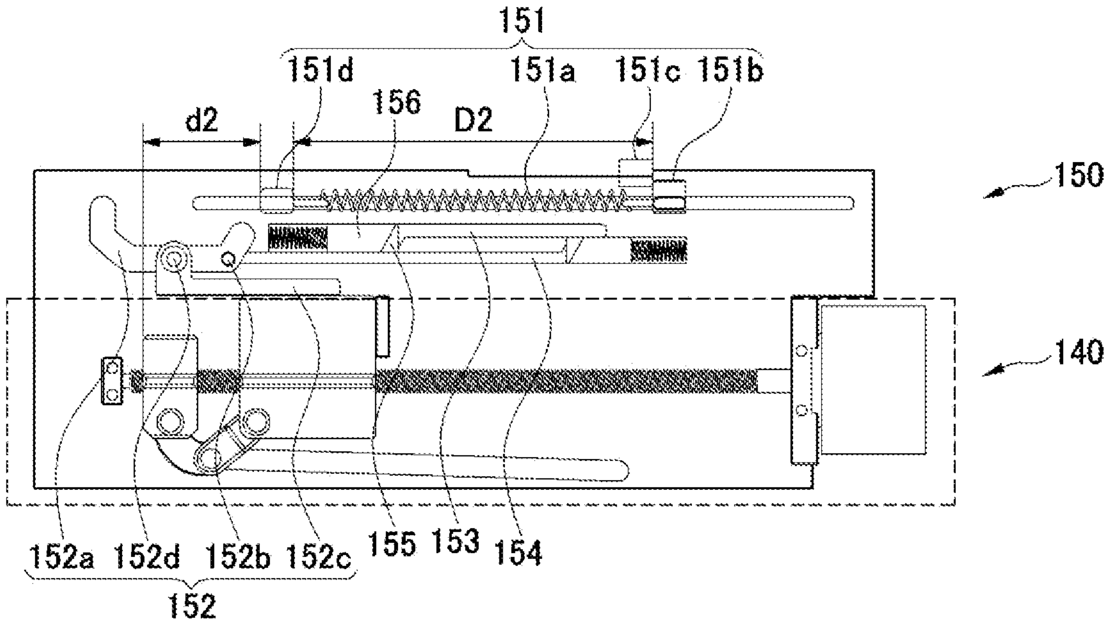
FIG. 6D illustrates an operation process of the electrode driving unit according to an embodiment of the present disclosure.

Referring to FIG. 6C and FIG. 6D, as the electrode guide 130 further moves in the forward direction after the tensile force maintenance unit 151 and the moving unit 152 are disconnected from each other, a tensile force may be generated in the first spring 151*a*. Since the tensile force is generated in the tensile force maintenance unit 151, the electrode unit 120 may be gradually brought into close contact with the tube V in the body as illustrated in FIG. 3B and FIG. 3C. Here, the electrode guide 130 illustrated in FIG. 3C may be in the second state.

Specifically, as illustrated in FIG. 6C, the pin 152*d* of the moving unit 152 moves together with the electrode guide driving unit 140 to the end of the path provided by the forward movement rail 153 and then moves along the connection rail 155, and the hinge 152*d* rotates. Thus, the connection portion 152*a* and the tensile force maintenance unit 151 may be disconnected from each other.

Even after the tensile force maintenance unit 151 and the moving unit 152 are disconnected from each other, the electrode guide driving unit 140 continues moving in the forward direction as illustrated in FIG. 6D, and the electrode connection portion 151*d* gradually moves in the forward direction along with forward movement of the electrode guide 130. Thus, the length of the first spring 151*a* may increase to a predetermined length (D1→D2) and a tensile force may be generated. Therefore, the electrode unit 120 may be gradually brought into close contact with the tube V in the body and may enclose the tube V in the body.

Here, the electrode guide driving unit 140 may be in a state where its forward movement is completed, and the electrode guide 130 may be in a state where the plurality of joint units 131 is completely drawn out along the curved winding path as illustrated in FIG. 3C.

That is, since the electrode guide 130 further moves in the forward direction after the tensile force maintenance unit 151 and the moving unit 152 are disconnected from each other, only the electrode connection portion 151*d* of the tensile force maintenance unit 151 may gradually move in the forward direction, and, thus, a distance between one side of the electrode connection portion 151*d* and one side of the electrode guide driving unit 140 may increase to a predetermined distance (d1→d2). Meanwhile, forward or backward movement of the electrode guide driving unit 140 can be controlled through the guide manipulation unit 113 to adjust the position of the tube V enclosed by the electrode unit 120 and the degree of close contact of the electrode unit 120 with the tube V in the body.

The electrode unit 120 in contact with the tube V in the body may transfer energy for damaging nerves, and, thus, neurotomy can be performed.

As the electrode connection portion 151*d* according to the present disclosure gradually moves in the forward direction, the electrode unit 120 may be gradually brought into close contact with the tube V in the body. Thus, it is possible to suppress damage to the tube V in the body when the electrode unit 120 is in close contact with the tube V in the body during neurotomy.

Also, the position of the tube V enclosed by the electrode unit 120 according to the present disclosure and the degree of close contact of the electrode unit 120 with the tube V in the body can be adjusted by controlling driving of the electrode guide driving unit 140 through the guide manipulation unit 113, and, thus, a surgical procedure can be performed on the tube V at an accurate position without damaging the tube V.

Figure 6E:
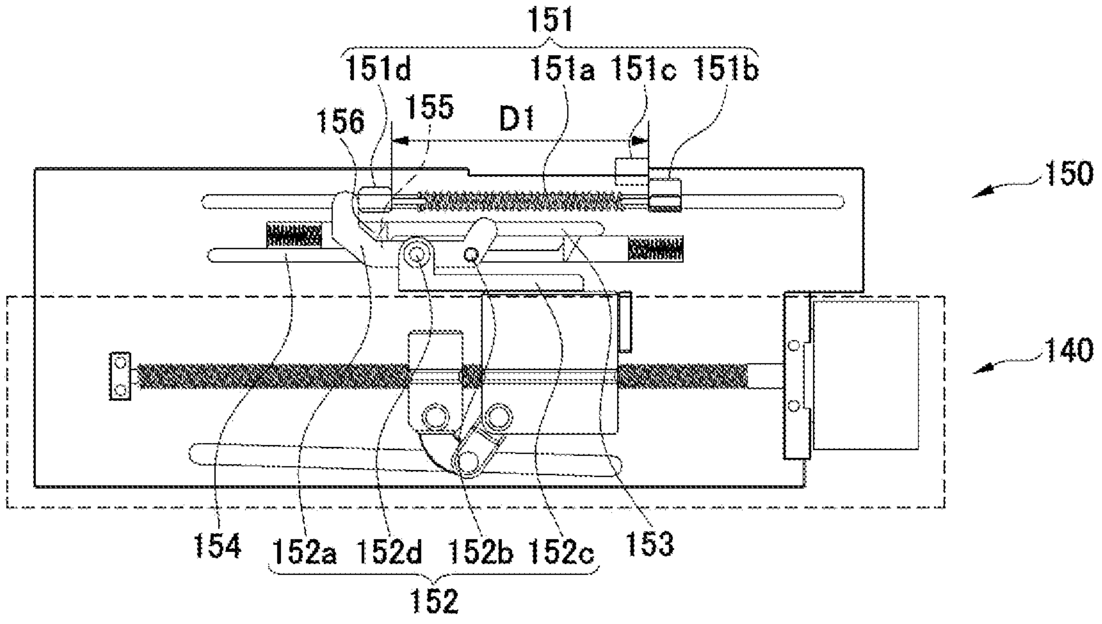
FIG. 6E illustrates an operation process of the electrode driving unit according to an embodiment of the present disclosure.
Figure 6F:
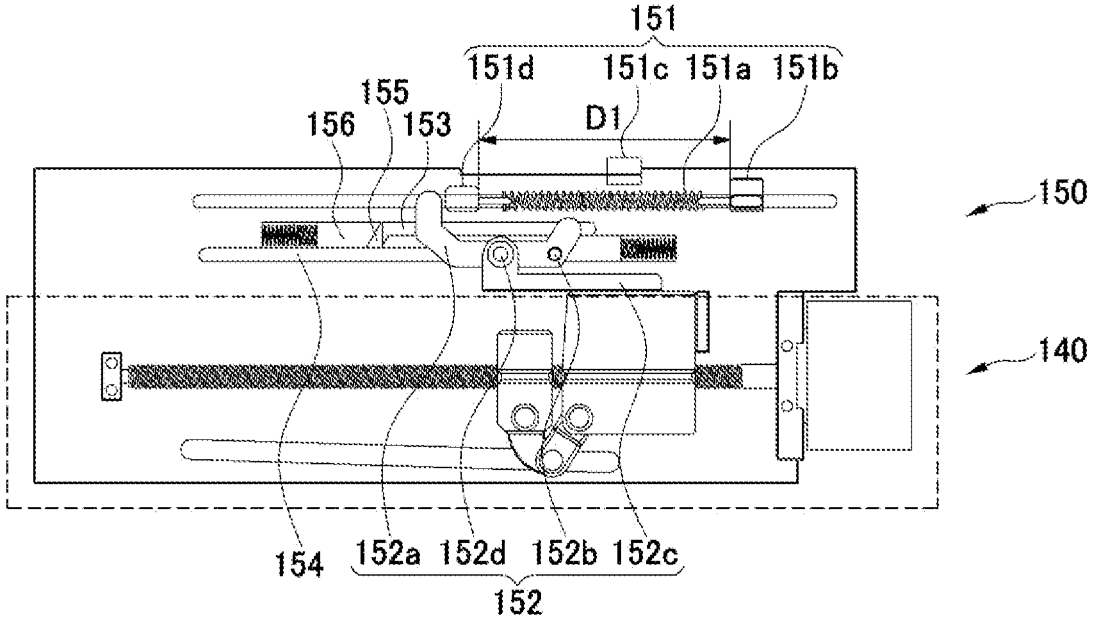
FIG. 6F illustrates an operation process of the electrode driving unit according to an embodiment of the present disclosure.

Then, referring to FIG. 6E and FIG. 6F, the electrode driving unit 150 may move the moving unit 152 in the backward direction through the electrode guide driving unit 140. Since the moving unit 152 and the electrode guide driving unit 140 move in the backward direction along the backward movement rail 154, it is possible to make the electrode guide 130 deviate from the circumference of the tube V in the body as illustrated in FIG. 3D.

Specifically, as illustrated in FIG. 6E, when the electrode guide driving unit 140 moves in the backward direction, the pin 152*b* of the moving unit 152 connected to the electrode guide driving unit 140 may move in the backward direction along the backward movement rail 154. Thus, the other side of the connection portion 152*a* meets the electrode connection portion 151*d* of the tensile force maintenance unit 151, which causes the tensile force maintenance unit 151 to move in the backward direction.

As the electrode connection portion 151*d* of the tensile force maintenance unit 151 moves in the backward direction together with the moving unit 152, the length of the first spring 151*a* may decrease to a predetermined length (D2→D1) and all the tensile force generated in the first spring 151*a* may be removed.

When the pin 152*b* moves in the backward direction, the electrode driving unit 150 blocks the connection rail 155 by means of the second stopper 156 to suppress the pin 152*b* not to move again along the connection rail 155. For example, the second stopper 156 may include a spring that compresses the second stopper 156 in order for the pin 152*b* to move along the connection rail 155 and returns the second stopper 156 back to its original state when the pin 152*b* is located on the backward movement rail 154.

As the electrode guide driving unit 140 and the electrode driving unit 150 move in the backward direction, the electrode unit 120 and the electrode guide 130 may move in a backward direction B toward the shaft 111 as illustrated in FIG. 3D.

When backward movement of the electrode guide driving unit 140 and the electrode driving unit 150 is completed, the pin 152*b* of the moving unit 152 may be located on the forward movement rail 153, i.e., in a standby state as illustrated in FIG. 6A. Here, the electrode unit 120 and the electrode guide 130 may also be in a standby state before protruding from the shaft 111 as illustrated in FIG. 3A.

Referring to FIG. 7, the electrode driving unit 150 according to another embodiment may further include a second spring 157 that connects the support 152*c* and the connection portion 152*a*. The electrode driving unit 150 may suppress the pin 152*b* not to move again along the connection rail 155 by using the second spring 157 when the pin 152*b* moves in the backward direction.

Therefore, the electrode driving unit 150 may suppress the pin 152*b* not to move again along the connection rail 155 when the pin 152*b* moves in the backward direction by using the second spring 157 connecting the support 152*c* and the connection portion 152*a* without a stopper that blocks the connection rail 155.

The above description of the present disclosure is provided for the purpose of illustration, and it would be understood by a person with ordinary skill in the art that various changes and modifications may be made without changing technical conception and essential features of the present disclosure. Thus, it is clear that the above-described embodiments are illustrative in all aspects and do not limit the present disclosure. For example, each component described as a single type may be implemented in a dispersed form, and likewise components described as distributed may also be implemented in a combined form.

The scope of the present disclosure is defined by the following claims rather than by the detailed description of the embodiment. It shall be understood that all modifications and embodiments conceived from the meaning and scope of the claims and their equivalents are included in the scope of the present disclosure.

The invention claimed is:

1. An electrode apparatus for nerve denervation or modulation in vivo, comprising:

a main body including a shaft;

an electrode unit formed to be drawn out from one end of the shaft and configured to denervate or modulate at least part of nerves on a tube in a body;

an electrode guide coupled to a first end of the electrode unit and configured to guide the electrode unit to be brought into contact with the tube in the body;

an electrode guide driving unit configured to move the electrode guide in forward and backward directions; and an electrode driving unit configured to move the electrode guide in the forward and backward directions in conjunction with the electrode guide driving unit, wherein the electrode driving unit includes:

a tensile force maintenance unit connected to a second end of the electrode unit different from the first end and configured to provide a tensile force to the electrode unit; and a moving unit that moves in the forward direction until the electrode guide is transitioned to a first state in a state where the moving unit is connected to the tensile force maintenance unit, and then is disconnected from the tensile force maintenance unit and further moves in the forward direction until the electrode guide is transitioned to a second state.

2. The electrode apparatus of claim 1, wherein as the electrode guide further moves in the forward direction after the tensile force maintenance unit is disconnected from the moving unit, the tensile force maintenance unit provides a tensile force to the electrode unit.

3. The electrode apparatus of claim 1, wherein the electrode apparatus is configured such that after the tensile force maintenance unit is disconnected from the moving unit and as the moving unit further moves in the forward direction, the electrode unit is brought into contact with the tube.

4. The electrode apparatus of claim 1, wherein the tensile force maintenance unit includes:

a first spring that provides a tensile force to the electrode unit.

5. The electrode apparatus of claim 4, wherein the tensile force maintenance unit further includes:

a protrusion protruding from one side; and a first stopper that blocks movement of the protrusion when the tensile force maintenance unit moves in the forward direction to generate the tensile force of the first spring.

6. The electrode apparatus of claim 1, wherein the moving unit further includes:

a connection portion for connection to the tensile force maintenance unit; and a pin formed in the connection portion and configured to enable the moving unit to move the tensile force maintenance unit in the forward direction, and the electrode driving unit further includes:

a forward movement rail along which the pin moves in the forward direction.

7. The electrode apparatus of claim 6, wherein the electrode driving unit further includes:

a backward movement rail along which the pin moves in the backward direction to transition the electrode guide from the second state to the first state.

8. The electrode apparatus of claim 7, wherein the backward movement rail has a greater length than the forward movement rail.

9. The electrode apparatus of claim 7, wherein the moving unit further includes:

a support connected to the electrode guide driving unit; and a hinge configured to make the connection portion rotate, and the electrode driving unit further includes:

a connection rail connecting the forward movement rail and the backward movement rail, and when the pin moves along the connection rail, the hinge rotates and the connection portion is disconnected from the tensile force maintenance unit.

10. The electrode apparatus of claim 9, wherein the electrode driving unit further includes:

a second spring that connects the support and the connection portion to suppress the pin not to move again along the connection rail when the pin moves in the backward direction.

11. The electrode apparatus of claim 9, wherein the electrode driving unit further includes:

a second stopper that blocks the connection rail when the pin is located on the backward movement rail through the connection rail in order to suppress the pin not to move again along the connection rail when the pin moves in the backward direction.

12. The electrode apparatus of claim 1, wherein in the first state, the electrode guide has not yet enclosed a circumference of the tube in the body, and in the second state, the electrode guide encloses the circumference of the tube in the body.

* * * * *